(12) United States Patent
Calderoni et al.

(10) Patent No.: US 10,338,259 B2
(45) Date of Patent: Jul. 2, 2019

(54) SURGICAL ADAPTER ASSEMBLIES AND WIRELESS DETECTION OF SURGICAL LOADING UNITS

(71) Applicant: Covidien LP, Mansfield, MA (US)

(72) Inventors: Anthony Calderoni, Bristol, CT (US);
John Pantazis, Stratford, CT (US);
Luis Dussan, East Haven, CT (US)

(73) Assignee: Covidien LP, Mansfield, MA (US)

( * ) Notice: Subject to any disclaimer, the term of this patent is extended or adjusted under 35 U.S.C. 154(b) by 372 days.

(21) Appl. No.: 15/371,279

(22) Filed: Dec. 7, 2016

(65) Prior Publication Data
US 2017/0168187 A1   Jun. 15, 2017

Related U.S. Application Data

(66) Substitute for application No. 62/266,791, filed on Dec. 14, 2015.

(51) Int. Cl.
*A61B 17/072*   (2006.01)
*G01V 3/10*   (2006.01)
(Continued)

(52) U.S. Cl.
CPC .............. *G01V 3/10* (2013.01); *A61B 17/072* (2013.01); *A61B 17/07207* (2013.01); *A61B 17/10* (2013.01); *A61B 17/1222* (2013.01); *A61B 17/3211* (2013.01); *A61B 90/98* (2016.02); *G01R 19/10* (2013.01); *G01R 23/02* (2013.01); *A61B 17/068* (2013.01); *A61B 2017/00017* (2013.01); *A61B 2017/00039* (2013.01); *A61B 2017/00115* (2013.01);
(Continued)

(58) Field of Classification Search
CPC ................ A61B 17/068; A61B 17/072; A61B 17/07207; A61B 17/115; A61B 17/1155; A61B 2017/00017; A61B 2017/00022; A61B 2017/00398; A61B 2017/0046; A61B 2017/00473; A61B 2017/00477; A61B 2017/00734; A61B 2017/00221; A61B 2017/2927; A61B 2017/07214
USPC .. 227/19, 175.1, 175.2, 176.1, 179.1, 180.1; 606/38, 139, 153, 219
See application file for complete search history.

(56) References Cited

U.S. PATENT DOCUMENTS 4,281,373 A   7/1981   Mabille
5,438,607 A   8/1995   Przygoda, Jr. et al.
(Continued)

FOREIGN PATENT DOCUMENTS

EP   2932910 A2   10/2015
WO   03013372 A2   2/2003

OTHER PUBLICATIONS

Extended European Search Report for EP 16 20 3836 dated Apr. 3, 2017.

*Primary Examiner* — Scott A Smith

(57) ABSTRACT

An adapter assembly includes an elongated body configured to couple to a handle assembly and a loading unit assembly. The adapter assembly includes an oscillator configured to output a voltage signal. A sensor determines a connection status of the loading unit assembly coupled to the adapter assembly based on a change in the voltage signal. The voltage signal includes a rectified voltage output and an induced voltage output and changes in response to the approximation of a winding disposed within a loading unit assembly to the oscillator.

19 Claims, 6 Drawing Sheets

(51) Int. Cl.
- *A61B 17/10* (2006.01)
- *A61B 17/122* (2006.01)
- *A61B 17/3211* (2006.01)
- *G01R 19/10* (2006.01)
- *G01R 23/02* (2006.01)
- *A61B 90/98* (2016.01)
- *A61B 17/068* (2006.01)
- *A61B 17/00* (2006.01)
- *A61B 90/00* (2016.01)

(52) U.S. Cl.
CPC ............... *A61B 2017/00221* (2013.01); *A61B 2017/00398* (2013.01); *A61B 2017/00464* (2013.01); *A61B 2017/00473* (2013.01); *A61B 2017/00477* (2013.01); *A61B 2017/07214* (2013.01); *A61B 2017/07285* (2013.01); *A61B 2090/0808* (2016.02)

(56) References Cited

U.S. PATENT DOCUMENTS

| | | |
|---|---|---|
| 6,423,001 B1 | 7/2002 | Abreu |
| 8,960,520 B2 | 2/2015 | McCuen |
| 9,421,003 B2* | 8/2016 | Williams .......... A61B 17/00234 |
| 9,839,480 B2* | 12/2017 | Pribanic ........... A61B 17/07207 |
| 10,164,466 B2* | 12/2018 | Calderoni .............. A61B 90/98 |
| 2007/0194913 A1 | 8/2007 | Yokoshima et al. |
| 2008/0164296 A1 | 7/2008 | Shelton et al. |
| 2011/0204119 A1* | 8/2011 | McCuen ........... A61B 17/07207 227/175.1 |
| 2011/0251606 A1* | 10/2011 | Kerr ................... A61B 18/1402 606/34 |
| 2014/0012237 A1 | 1/2014 | Pribanic et al. |
| 2015/0303996 A1* | 10/2015 | Calderoni .............. A61B 90/98 307/104 |
| 2015/0351765 A1 | 12/2015 | Valentine et al. |
| 2016/0354071 A1 | 12/2016 | Williams et al. |
| 2017/0007252 A1 | 1/2017 | Williams et al. |

* cited by examiner

SURGICAL ADAPTER ASSEMBLIES AND WIRELESS DETECTION OF SURGICAL LOADING UNITS

CROSS-REFERENCE TO RELATED APPLICATIONS

This application claims the benefit of and priority to U.S. Provisional Patent Application No. 62/266,791 filed Dec. 14, 2015, the entire disclosure of which is incorporated by reference herein.

BACKGROUND

1. Technical Field

The present disclosure relates to adapter assemblies and surgical loading units for use with an electromechanical surgical system and their methods of use. More specifically, the present disclosure relates to hand-held, electromechanical surgical instruments capable of detecting the presence of a loading unit and/or identifying one or more parameters of a loading unit attached to an adapter assembly.

2. Background of Related Art

Linear clamping, cutting, and stapling surgical devices may be employed in surgical procedures to resect tissue. Conventional linear clamping, cutting, and stapling devices include a handle assembly, an elongated shaft and a distal portion. The distal portion includes a surgical loading unit which may contain pair of gripping members that clamp about the tissue.

A need currently exists for a contactless detection assembly between the surgical loading unit and the adapter assembly for the electromechanical surgical system. With the removal of a physical contact for detection between the surgical loading unit and adapter assembly, there is a decreased degradation of the exposed identification components of the surgical loading unit during use and/or over multiple sterilization processes.

SUMMARY

The present disclosure relates to an adapter assembly, including an elongated body having a proximal portion and a distal portion, wherein the proximal portion is configured to couple to a handle assembly and the distal portion is configured to couple to a loading unit assembly. The adapter assembly includes an oscillator disposed within the elongated body and configured to output a voltage signal. A sensor disposed within the adapter assembly determines a connection status of a loading unit assembly coupled to the adapter based on a change in the voltage signal.

In further embodiments, the voltage signal output by the oscillator includes a rectified voltage output and an induced voltage output.

In another embodiment, the oscillator is a Colpitts Oscillator.

In a further embodiment, the voltage signal changes in response to approximation of a winding disposed within a loading unit to the oscillator or in response to a wireless interaction with a winding disposed within a loading unit.

In other embodiments, the sensor is further configured to determine at least one parameter of the loading unit assembly based on the change in the voltage signal.

In other embodiment, the at least one parameter of the loading unit assembly is selected from the group consisting of a serial number of a loading unit assembly, a type of a loading unit assembly, a size of a loading unit assembly, a fastener size, a fastener type, prior use information, and maximum number of uses of a loading unit assembly.

In another embodiment, a method for wireless detection of a surgical loading unit being coupled to an adapter assembly is disclosed. The method includes applying an input voltage and frequency to an oscillator circuit disposed within an adapter assembly and measuring at least one parameter of the oscillator circuit. The method additionally includes inserting the surgical loading unit containing a winding into the adapter assembly, thereby altering the at least one parameter and measuring the altered at least one parameter. The method further determines a difference between the at least one parameter and the altered at least one parameter and determining presence of the surgical loading unit based on the difference.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
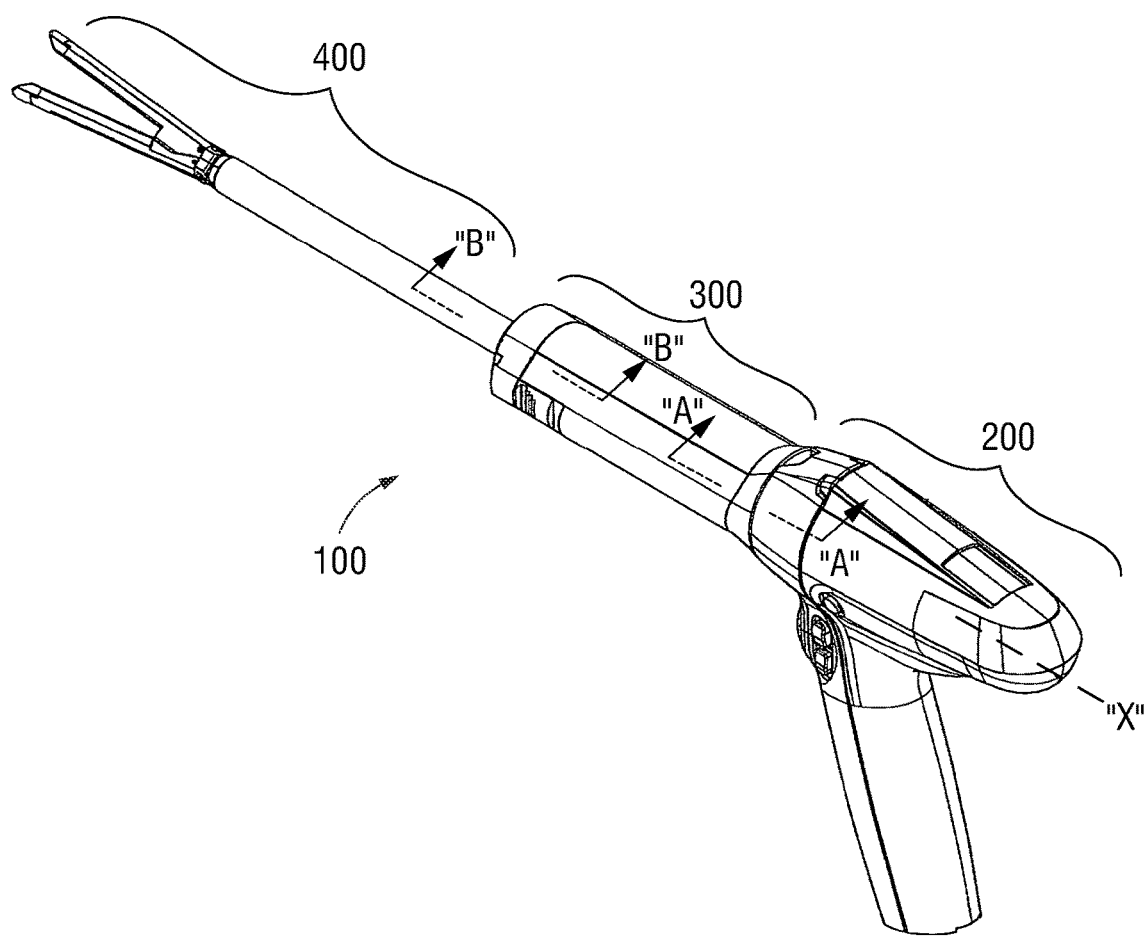
FIG. 1 is a perspective view of an electromechanical surgical instrument according to an embodiment of the present disclosure.

Embodiments of the presently disclosed surgical devices, adapter assemblies, and surgical attachments are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

With reference to FIG. 1, a surgical device 100, in accordance with an embodiment of the present disclosure, is a powered hand held electromechanical surgical device configured for selective attachment thereto of a plurality of different end effectors. The end effectors may be any one of various surgical attachments including, but not limited to, a surgical stapler, a surgical cutter, a surgical stapler-cutter, a linear surgical stapler, a linear surgical stapler-cutter, a circular surgical stapler, a circular surgical stapler-cutter, a surgical clip applier, a surgical clip ligator, a surgical clamping device, a vessel expanding device, a lumen expanding device, a scalpel, a fluid delivery device or any other suitable type of surgical instrument. Each of the surgical attachments is configured for actuation and manipulation by the powered hand held electromechanical surgical device 100.

Figure 3:
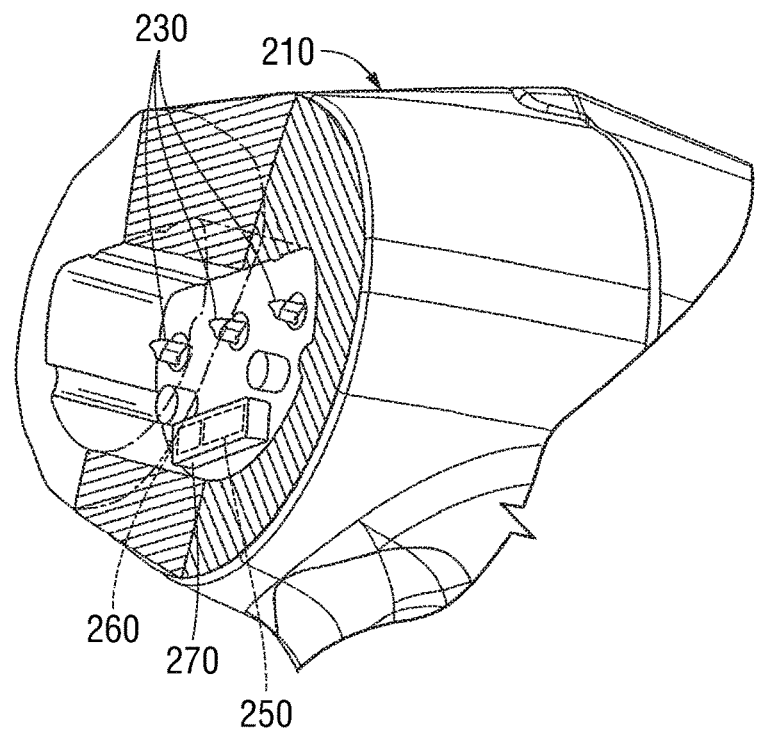
FIG. 3 is a perspective view of a handle connector port of a handle assembly of the surgical instrument shown in FIG. 1.
Figure 4:
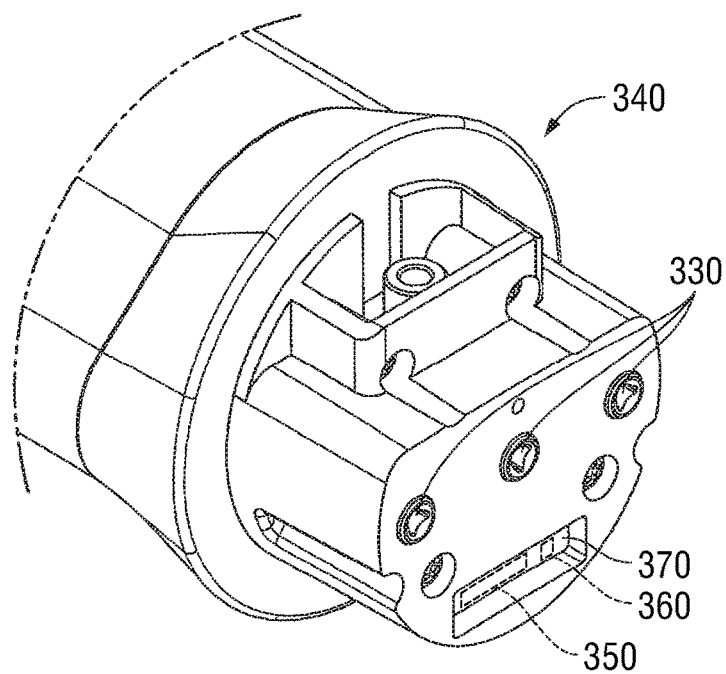
FIG. 4 is a perspective view of an adapter connector port of an adapter assembly of the surgical instrument shown in FIG. 1.

As illustrated in FIG. 1, the surgical instrument 100 includes handle assembly 200 configured for selective connection with an adapter assembly 300 (see FIG. 3), and, in turn, adapter assembly 300 is configured for selective connection with a surgical loading unit 400 (e.g., an end effector, multiple or single-use loading unit, see FIG. 4) that is configured to perform at least one function. Handle assembly 200 is configured and adapted to actuate adapter assembly 300. Adapter assembly 300 is connectible with surgical loading unit 400, as described herein. Surgical instrument 100 further defines a longitudinal axis "X."

Figure 2:
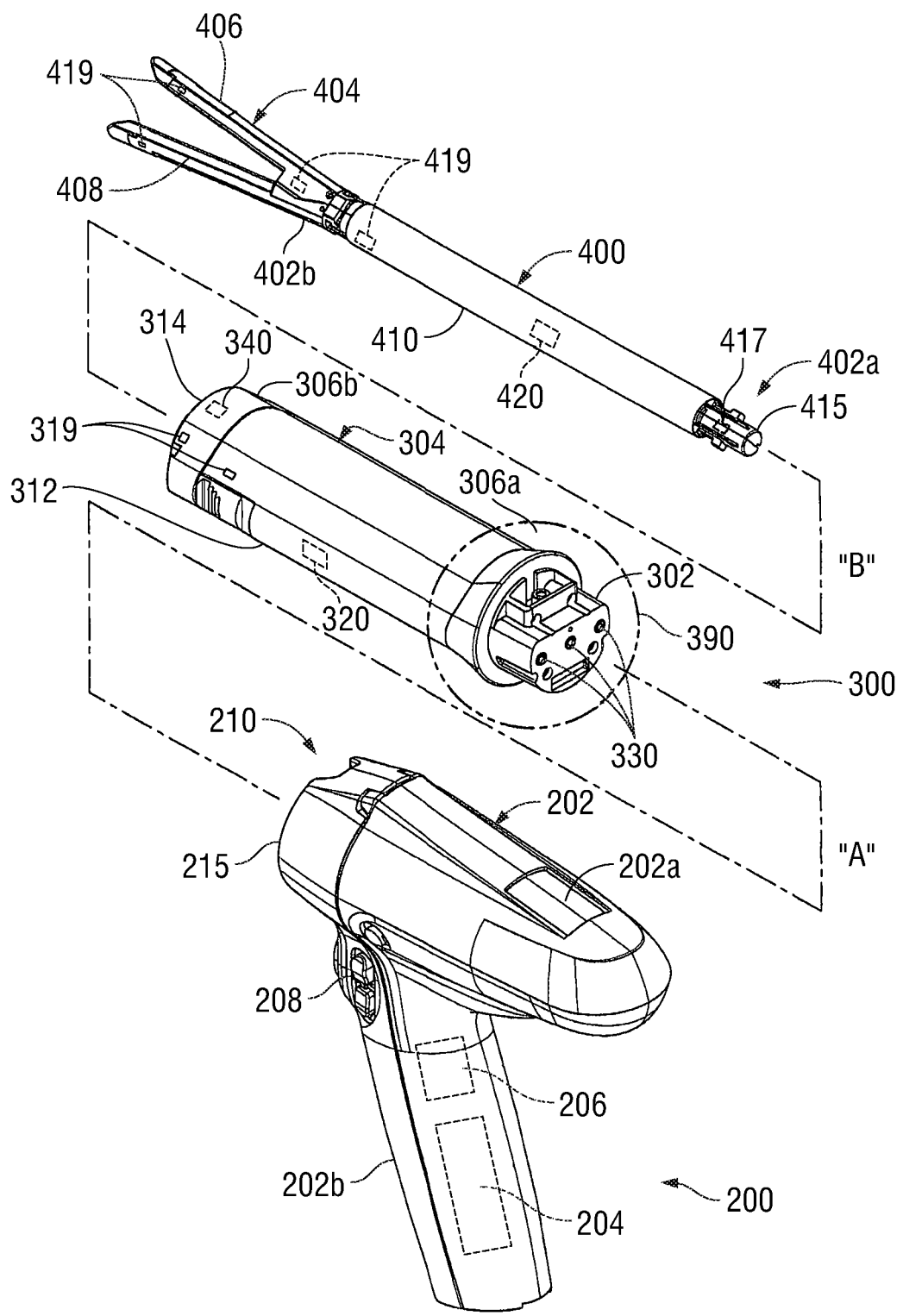
FIG. 2 is a perspective view of the surgical instrument of FIG. 1 with components separated.

For a detailed description of the construction and operation of an exemplary electromechanical, hand-held, powered surgical instrument reference may be made to U.S. Pat. No. 7,819,896, International Publication No. WO 2009/039506 and U.S. Publication No. 2011/0121049, the entire contents of which of each are incorporated herein by reference, FIG. 2 shows each of handle assembly 200, adapter assembly 300, and surgical loading unit 400 and the connectivity between therein. Handle assembly 200 includes a handle housing 202 having a controller 204 and a drive mechanism 215 disposed therein. The controller 204 is configured to control the various operations of surgical instrument 100. Handle housing 202 also defines a cavity therein (not shown) for selective removable receipt of a power source, such as a rechargeable battery (not shown). The power source is configured to supply power to any of the electrical components of handle assembly 200 including electric motors 206 used to drive the operation of surgical loading unit 400 via adapter assembly 300.

Handle assembly 200 further includes gear selector boxes (not shown), and gearing mechanisms (not shown) coupled to the motors 206. Controller 204 is configured to control motors 206 based on the presence of a loading unit, for example, surgical loading unit 400 coupled to the handle assembly 200 by the adapter assembly 300. Handle assembly 200 further includes a control assembly 208, which may include one or more finger-actuated control buttons, rocker devices, joystick or other directional controls, whose input is transferred to the drive mechanism 215 to actuate adapter assembly 300 and in turn surgical loading unit 400.

In particular, drive mechanism 215 is configured to drive shafts and/or gear components in order to selectively move an end effector 404 of surgical loading unit 400 and to rotate end effector 404 about longitudinal axis "X" defined by surgical instrument 100 as shown in FIGS. 3 and 4

Handle assembly 200 further includes a nose or connecting portion 210 configured to accept a corresponding adapter connector port 390 of adapter assembly 300. Connecting portion 210 of handle assembly 200 is configured to receive adapter connector port 390 of adapter assembly 300 when adapter assembly 300 is mated to handle assembly 200 (see FIG. 3).

Connecting portion 210 houses one or more drive shafts 230 (FIG. 3) that interface with corresponding one or more input shafts 330 (FIGS. 2 and 4) of adapter assembly 300. Connecting portion 210 further includes a planar face and a substantially circular configuration. In some embodiments, connecting portion 210 has alternative configurations, such as, for example, oval, oblong, triangular, square, rectangular, hexagonal, polygonal, or star-shaped, configured for mating engagement with adapter connector port 390 of adapter assembly 300. The mating of handle assembly 200 with adapter assembly 300 allows rotational forces to be independently transmitted.

Handle housing 202 of handle assembly 200 includes an upper housing portion 202a which houses various components of hand-held electromechanical surgical device 200, and a lower hand grip portion 202b extending from upper housing portion 202a. Lower hand grip portion 202b may be disposed distally of a proximal-most end of upper housing portion 202a. In some embodiments, lower hand grip portion 202b has various surface features, such as, for example, knurled, smooth, rough, and/or textured to enhance a practitioner's gripping of lower hand grip portion 202b.

In some embodiments, handle assembly 200 may include a display (not shown) configured to display information from the data signals received from adapter assembly 300 and surgical loading unit 400 for use by a user of the surgical instrument 100.

With continued reference to FIG. 2, the adapter connector port 390 of the adapter assembly 300 includes a knob housing 302. The adapter assembly 300 also includes an elongated body 304 extending from a distal end of knob housing 302. Knob housing 302 and elongated body 304 are configured and dimensioned to house the components of adapter assembly 300. Elongated body 304 may be dimensioned for endoscopic insertion. For example, elongated body 304 may be passable through a typical trocar port, cannula or the like. Knob housing 302 is dimensioned to remain outside a trocar port, cannula of the like.

Adapter connector port 390 is configured to mateably connect with connecting portion 210 of handle assembly 200 and includes one or more input shafts 330 configured to interface with corresponding one or more drive shafts 230 of connecting portion 210 of handle assembly 200 (FIGS. 3 and 4).

Adapter connector port 390 is configured to connect with connecting portion 210 includes one or more input shafts 330 extending therefrom, and defines a recess 370 formed therein, which is sized and configured to receive protrusion 270 of handle connector port 210. One or more input shafts 330 are configured to rotatably interface with one or more drive shafts 230 of handle connector port 210. In some embodiments, adapter connector port 390 may also include primary distal coil 350 and additional coils 360 positioned within recess 370.

Elongated body 304 has a distal portion 306b configured to be coupled to proximal portion 402a of surgical loading unit 400. Elongated body 304 further includes a cylindrical outer housing 312 and a cylindrical inner housing 314 disposed therein.

Figure 6:
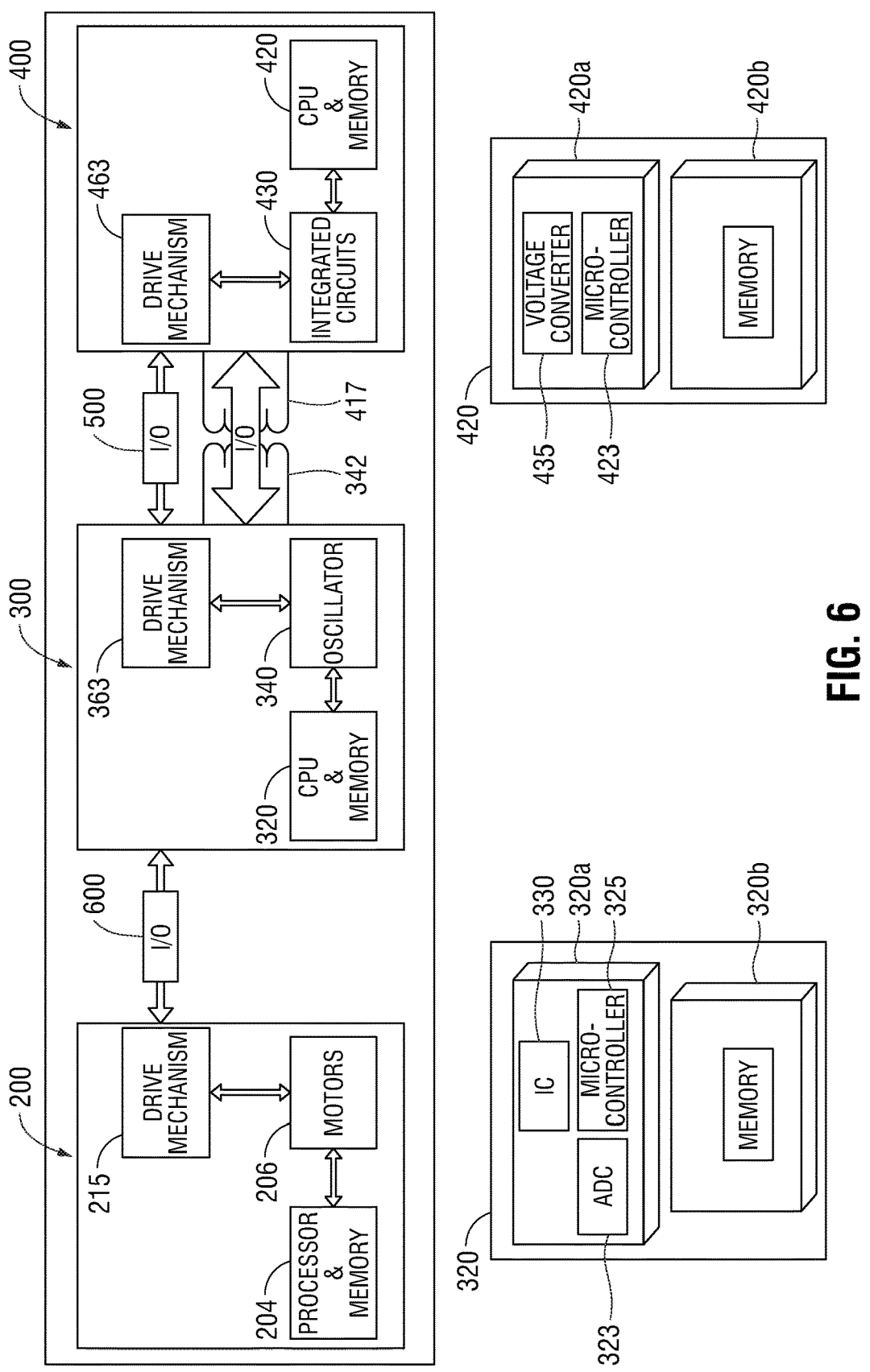
FIG. 6 is a schematic connectivity diagram of each of the components of the surgical instrument of FIG. 1.

A controller 320 is disposed within or on cylindrical inner housing 314 (FIG. 6). In addition, oscillator 340 is located within cylindrical inner housing 314 at distal portion 306b of adapter assembly 300, as further detailed and described herein.

Adapter assembly 300 may also include a plurality of sensors 319 disposed thereabout. Sensors 319 of adapter assembly 300 are coupled to controller 320 and are configured to detect various conditions of adapter assembly 300 and provide input to controller 320 in the form of data signals.

With continued reference to FIG. 2, surgical loading unit 400 has a proximal portion 402a and is configured for engagement with distal end 306b of elongated body 304 of adapter assembly 300. Surgical loading unit 400 includes a distal portion 402b having an end effector 404 extending therefrom. End effector 404 is pivotally attached to distal portion 402b. End effector 404 may include an anvil assembly 408 and a cartridge assembly 406. Cartridge assembly 406 is pivotable in relation to anvil assembly 408 and is movable between an open or unclamped position and a closed or clamped position for insertion through a cannula of a trocar.

Surgical loading unit 400 further includes a housing 410 configured to contain the drive mechanisms, integrated circuits, processors, and memory for controlling end effector 404. In particular, surgical loading unit 400 further includes a controller 420 disposed within or on inner housing 410b and loading winding 417 located at proximal portion 402a, as further detailed and described herein.

Surgical loading unit 400 may also include a sensors 419 disposed thereabout. Sensors 419 of the surgical loading unit 400 may be substantially similar to sensors 319 of adapter 300 and are configured to detect various conditions of surgical loading unit 400 or of the environment (e.g., if the end effector 404 is open, thickness of tissue within the end effector 404, the temperature within the surgical loading unit 400, etc.). Sensors 419 provide input to controller 420 in the form of data signals.

Referring now to FIGS. 3 and 4, components of connecting portion 210 of handle assembly 200 and adapter connector port 390 of adapter assembly 300 are shown.

Connecting portion 210 of handle assembly 200 includes a protrusion 270 extending distally therefrom. In some embodiments, a proximal coil 250 is disposed within protrusion 270 of connecting portion 210 of handle assembly 200. Protrusion 270 may also include includes additional coils 260 adjacent to, but electrically shielded from the proximal coil 250.

As described herein adapter connector port 390 is configured to mateably connect with connecting port 210.

Figure 5:
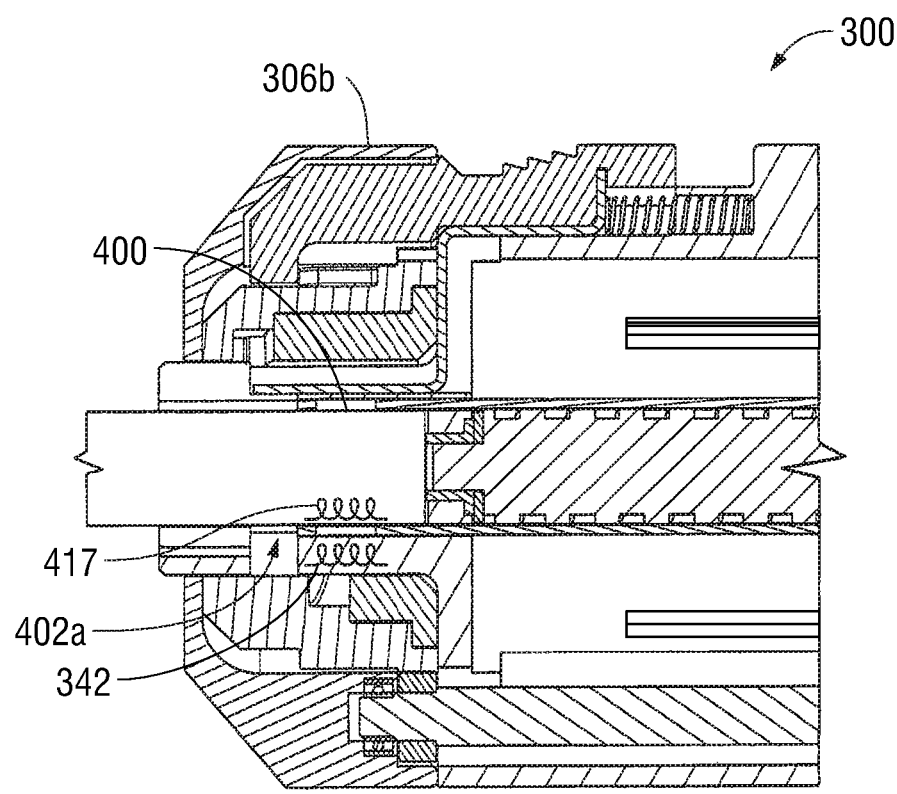
FIG. 5 is a cross sectional view of the adapter assembly of FIG. 1 taken along a section line "B-B" of FIG. 1.

Referring now to FIG. 5, surgical loading unit 400 and adapter assembly 300 are shown in an inserted and engaged position. In use, surgical loading unit 400 is inserted within the distal end of elongated tube 304 of adapter assembly 300. In some embodiments, surgical loading unit 400 may be rotated in a clockwise or counter-clockwise direction thereby locking surgical loading unit 400 in position. Once inserted and engaged, distal portion 306b of the adapter assembly 300 is located within proximal portion 402a of loading unit 400.

Figure 7:
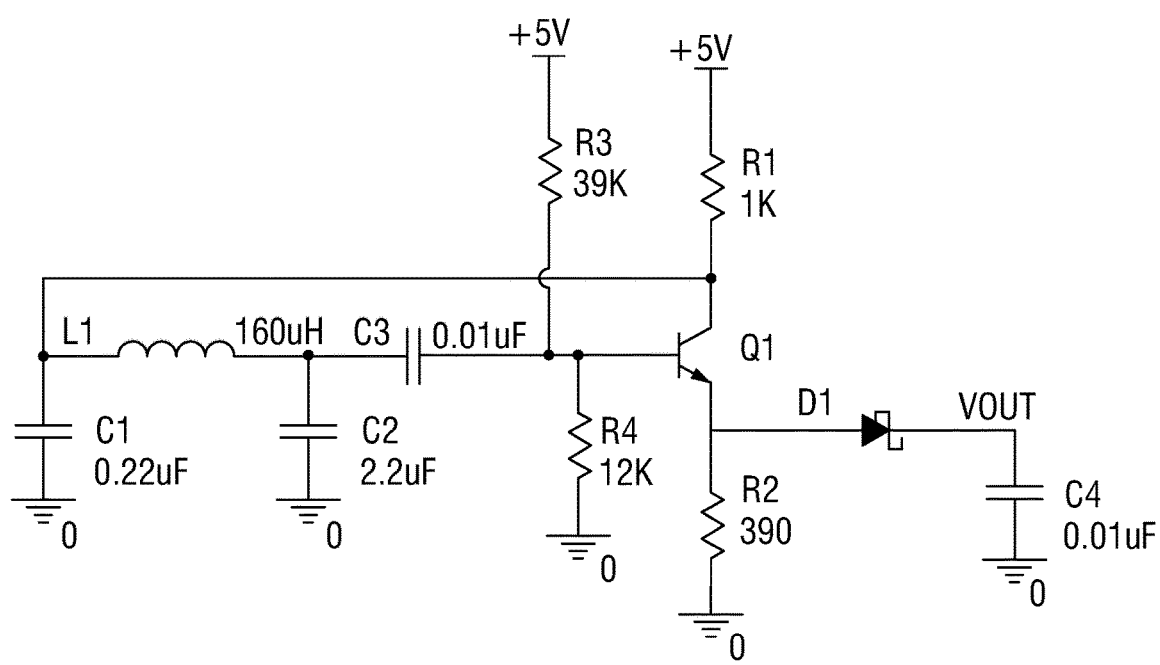
FIG. 7 is a circuit diagram of an oscillator of the adapter assembly of FIG. 1.

Upon insertion and engagement, loading winding 417 of surgical loading unit 400 inductively couples to oscillator winding 342 of oscillator 340 (FIGS. 6 and 7). It is also contemplated that once engaged, the magnetic field produced by the oscillating current in oscillator winding 342 energizes loading winding 417 as described below. Once energized, loading winding 417 (via a connection with integrated circuits 430 and controller 420) is able to provide energy wirelessly to surgical loading unit 400 (FIG. 5).

Once surgical loading unit 400 and adapter assembly 300 are coupled to each other, a wireless interface 500 (FIG. 6) is created between surgical loading unit 400 and adapter assembly 300. As used herein "wireless interface" denotes a non-contact interface that is capable of transmitting energy from adapter assembly 300 to surgical loading unit 400 and transmitting data signals between adapter assembly 300 and surgical loading unit 400. It is also contemplated that control signals may be transmitted via wireless interfaces 500 and 600 from handle assembly 200 to loading unit 400 via adapter assembly 300.

Additionally and as further described in description of FIG. 7, inductive coupling of loading winding 417 to oscillator winding 342 changes the overall impedance of oscillator winding 342, which also changes the amplitude of the sinusoidal voltage output. The present disclosure provides for determining whether the surgical loading unit 400 is inserted into adapter 300 as well as identifying the type of surgical loading unit based on the change in amplitude of the voltage waveform passing through the oscillator 340.

Referring now to FIG. 6, a diagram of the connectivity between handle assembly 200, adapter assembly 300, and surgical loading unit 400, and each of their internal components is shown.

As described above, handle assembly 200 includes a controller 204, one or more motors 206, and drive mechanism 215. Controller 204 is configured to control one or more motors 206 and drive mechanism 215. Once handle assembly 200 is engaged with adapter assembly 300, the wireless interface 600 provides for the input and output transmission of data signals between handle assembly 200 and adapter assembly 300. Interface 600 may also be created using induction coils or any other RF transceivers suitable for transmitting data signals and/or energy wirelessly.

The controller 320 of the adapter assembly 300 includes processor 320a and memory 320b. The memory 320b may be one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. Memory 320b is configured to store one or more parameters relating to adapter assembly 300. Processor 320a is further configured to include analog to digital converter (ADC) 323 of a microcontroller 325 which is coupled to an integrated circuit 330 within adapter 300. The processor 320a may be any suitable logic unit (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), an application specific integrated circuit (ASIC), or discrete logic circuitry, a microprocessor, and combinations thereof.

Integrated circuit 330 contains and/or is coupled to an oscillator 340 capable of interfacing with the surgical loading unit 400 once adapter 300 is engaged. In one embodiment, oscillator 340 is a Colpitts Oscillator as shown in FIG. 7, an inductor/capacitor circuit which controls the frequency of oscillations and consists of a single inductor and two capacitors in series.

Oscillator 340 contains one of more oscillator windings 342 which are disposed within cylindrical inner housing 314 of adapter assembly 300 (FIG. 2) and are configured to interface with one or more loading winding 417 disposed within surgical loading unit 400 upon insertion of surgical loading unit 400 into adapter assembly 300.

Controller 420 of surgical loading unit 400 includes loading unit processor 420a and memory 420b. Processor 420a and memory 420b may be substantially similar to the processor 320a and memory 320b as described above. Memory 420b is configured to store one or more parameters relating to surgical loading unit 400. The parameter may include at least one of a serial number of a loading unit assembly, a type of a loading unit assembly, a size of a loading unit assembly, a fastener size, a fastener type, prior use information, and maximum number of uses of a loading unit assembly, and combinations thereof. Memory 420b is configured to communicate to handle assembly 200 and adapter 300 a presence of surgical loading unit 400 and one or more of the parameters of surgical loading unit 400 described herein, upon engagement of surgical loading unit 400 with adapter assembly 300.

Loading unit processor 420a may include a voltage to current converter 423 that converts data signals of the plurality of sensors 419 to high frequency signals for transmission across interface 500 as detailed herein. Loading unit processor 420a further includes a microcontroller 435 which is coupled to an integrated circuit 430 within surgical loading unit 400. Loading unit processor 420a is further configured to transmit data signals via interface 500 to adapter assembly 300. It is contemplated that the loading unit processor 420a may be directly wired to loading winding 417.

Loading winding 417 is configured to interface with oscillator winding 342 of oscillator 340 once surgical loading unit 400 is engaged to the adapter assembly 300. Once engaged, loading winding 417 is energized via the connection with oscillator windings 342 and able to power one or more integrated circuits 430 and/or controller 420 contained therein. Integrated circuits 430 may be identification integrated chips (i.e., a 1-Wire chip), sensors 419, and any other circuits. It is contemplated that one or more integrated circuits 430 may be powered by loading winding 417.

Once loading winding 417 and oscillator winding 342 are coupled, a signal passing through the oscillator winding 342 is modified. In particular, the amplitude of the voltage of the signal is modified. In further embodiments, other parameters of the signal may also be modified, such as its frequency. The processor 320a is configured to detect the presence of the surgical loading unit 400 based on the change in a parameter of the signal, such as its amplitude and/or its frequency. In addition, processor 320a is capable of identifying the surgical loading unit. The controller 320 and/or the processor 320a are configured to analyze the change in the parameter of the signal and compare the change in the parameter to a plurality of changes in the parameter stored in memory 320b. In particular, the memory 320b includes a look-up table which matches the stored changes in the parameters of the signal to specific surgical loading units 400. Thus, if there is a match, the controller 320 may then identify the surgical loading unit 400 based on the detected change in the parameter of the signal. In addition, the controller 320 is also configured to determine other properties of the surgical loading unit 400. In embodiments, this information may be transmitted via the wireless interface 600 to handle assembly 400.

Referring now to FIG. 7, an example circuit diagram of oscillator 340 is shown using a Colpitts Oscillator. Although FIG. 7 includes specific numeric values for each of the components, the specific values are included for illustrative purposes.

Oscillator 340 is used to produce a voltage sine wave whose amplitude, once surgical loading unit 400 is engaged with adapter assembly 300, namely, once loading winding 417 is inductively coupled to oscillator winding 342. Oscillator 340 is driven by an inductor ($L_1$) and capacitors ($C_1$ and $C_2$) whose values determine the frequency ($f_r$) of the output voltage signal ($V_{out}$). As stated above and shown in FIG. 5, as loading winding 417 ($L_2$) is engaged with oscillator winding 342 ($L_1$), the total value of inductance ($L_{tot}$) is changed thereby altering the frequency ($f_r$), via mutual inductance. Formulas (1), (2), and (3) describe the total capacitance, frequency of the oscillator circuit, and changes in inductance.

$$C_{TOT} = \frac{C_1 C_2}{C_1 + C_2} \quad (1)$$

Formula (1) describes the total capacitance ($C_{tot}$) of the oscillator circuit, and is based on the two capacitors ($C_1$ and $C_2$) in series. The total capacitance ($C_{tot}$) is used in determination of the frequency ($f_r$) of the output voltage ($V_{out}$).

$$f_r = \frac{1}{2\pi \sqrt{L_{Tot} C_{TOT}}} \quad (2)$$

Formula (2) describes the frequency of the output voltage ($V_{out}$) and is based on the values of $L_{tot}$ and $C_{tot}$ of formula (1). In the case where loading winding 417 ($L_2$, not shown) is not engaged with oscillator winding 342 ($L_1$), total inductance ($L_{tot}$) remains equal to the value of inductor ($L_1$).

$$L_{TOT} = \sqrt{L_1 L_2} \quad (3)$$

Formula (3) described the total inductance ($L_{tot}$) once loading winding 417 ($L_2$, not shown) is engaged with oscillator winding 342 ($L_1$). Using the altered total inductance ($L_{tot}$) value based on varying loading winding 417 ($L_2$, not shown) causes a change of frequency ($f_r$), which can be measured by analog to digital converter (ADC) 323 of a microcontroller 325.

In some embodiments, it is contemplated that various types of surgical loading units each include a distinct loading winding 417 ($L_2$) which, once engaged with oscillator winding 342 ($L_1$), change the frequency ($f_r$) in such a manner that it can be determined the type of surgical loading unit engaged based on the change in frequency ($f_r$).

In use, oscillator 340 is provided an input signal at a specific voltage and frequency. In an exemplary embodiment, as shown in FIG. 7, an input voltage of +5V is provided to the oscillator 340. Based on this input voltage, a first, namely, an unaltered parameter, of the input signal is measured. As noted above, the parameter may be the signal's output voltage, frequency, or combinations thereof. The loading winding 417 of the surgical loading unit 400 is then coupled with oscillator winding 342 of the oscillator 340 of the adapter assembly 300. Upon coupling loading winding 417 with oscillator winding 342, one or both of the output voltage and output frequency of the signals is altered based on the mutual inductance between oscillator winding 342 and loading winding 417. Once coupled, the signal parameters are measured again and compared to the previously measured unaltered parameters, to determine a difference therebetween. The measured difference may then be used to determine the presence of and/or identity of the surgical loading unit 400.

Surgical instruments according to the present disclosure may also be configured to work with robotic surgical systems, such as telesurgery systems. Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. An adapter assembly, comprising:
    an elongated body having a proximal portion and a distal portion, wherein the proximal portion is configured to couple to a handle assembly and the distal portion is configured to couple to a loading unit assembly;
    an oscillator disposed within the elongated body and configured to output a voltage signal; and
    a sensor disposed within the elongated body and configured to determine a connection status of a loading unit assembly coupled to the elongated body based on a change in the voltage signal.

2. The adapter assembly according to claim 1, wherein the voltage signal includes a rectified voltage output and an induced voltage output.

3. The adapter assembly according to claim 1, wherein the oscillator is a Colpitts Oscillator.

4. The adapter assembly according to claim 1, wherein the voltage signal changes in response to the approximation of a winding disposed within a loading unit assembly to the oscillator.

5. The adapter assembly according to claim 1, wherein the voltage signal changes in response to a wireless interaction with a winding disposed within a loading unit.

6. The adapter assembly according to claim 1, wherein the sensor is further configured to determine at least one parameter of a loading unit assembly based on the change in the voltage signal.

7. The adapter assembly according to claim 6, wherein the at least one parameter is selected from the group consisting of a serial number of a loading unit assembly, a type of a loading unit assembly, a size of a loading unit assembly, a fastener size, a fastener type, prior use information, and maximum number of uses of a loading unit assembly.

8. A surgical instrument comprising:
    a handle assembly including a processor and a memory, wherein the processor is configured to control a motor;
    a surgical loading unit including:
        a memory configured to store at least one parameter of the surgical loading unit; and
        a winding; and
    an adapter assembly configured to couple to the handle assembly and the surgical loading unit, the adapter assembly including:
        an oscillator configured to wirelessly couple to the winding and to output a voltage signal; and
        a sensor configured to determine a connection status of the surgical loading unit based on a change in the voltage signal due to wireless coupling of the winding and the oscillator.

9. The surgical instrument according to claim 6, wherein the at least one parameter of the surgical loading unit is an identifier of the surgical loading unit.

10. The surgical instrument according to claim 6, wherein the oscillator is a Colpitts Oscillator.

11. The surgical instrument according to claim 6, wherein the change in the voltage signal is a change in frequency.

12. The surgical instrument according to claim 6, wherein the sensor is further configured to determine at least one parameter of the surgical loading unit assembly based on the change in the voltage signal.

13. The surgical instrument according to claim 12, wherein the at least one parameter is selected from the group consisting of a serial number of the surgical loading unit assembly, a type of the surgical loading unit assembly, a size of the surgical loading unit assembly, a faster size, a fastener type, prior use information, and maximum number of uses of the surgical loading unit.

14. The surgical instrument according to claim 6, wherein the voltage signal includes a rectified voltage output and an induced voltage output.

15. A method for wireless detection of a surgical loading unit being coupled to an adapter assembly, the method comprising:
    generating a signal at an oscillator circuit disposed within an adapter assembly;
    measuring at least one parameter of the oscillator circuit;
    inserting a surgical loading unit including a winding into the adapter assembly, thereby altering the at least one parameter;
    measuring the altered at least one parameter;
    determining a difference between the at least one parameter and the altered at least one parameter; and
    determining presence of the surgical loading unit based on the difference.

16. The method according to claim 15, wherein the at least one parameter is a voltage or a frequency of the signal.

17. The method according to claim 15, wherein altering the oscillator parameter is based on a wireless connection between the winding of the surgical loading unit and the oscillator circuit of the adapter assembly.

18. The method according to claim 15, further comprising determining at least one operational parameter of the surgical loading unit based on the difference.

19. The method according to claim 18, wherein determining the at least one operational parameter of the surgical loading unit includes identifying the surgical unit.

* * * * *